(12) United States Patent
Vogel et al.

(10) Patent No.: US 7,611,903 B2
(45) Date of Patent: Nov. 3, 2009

(54) SYSTEM FOR TRAPPING AND STORING GASES FOR SUBSEQUENT CHEMICAL REDUCTION TO SOLIDS

(75) Inventors: John S. Vogel, San Jose, CA (US); Ted J. Ognibene, Oakland, CA (US); Graham S. Bench, Livermore, CA (US); Graham F. Peaslee, Holland, MI (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 1290 days.

(21) Appl. No.: 10/241,301

(22) Filed: Sep. 11, 2002

(65) Prior Publication Data

US 2004/0047766 A1    Mar. 11, 2004

(51) Int. Cl.
*G01N 33/00* (2006.01)
(52) U.S. Cl. .......................... 436/177; 422/50; 422/55; 422/58; 422/83; 422/88; 422/99; 422/101; 422/102; 422/103; 436/83; 436/81; 436/137; 436/145
(58) Field of Classification Search .................. 422/50, 422/55, 58, 83, 86, 88, 99, 101, 102, 103; 436/83, 81, 137, 145, 146, 177
See application file for complete search history.

(56) References Cited

U.S. PATENT DOCUMENTS

| | | | |
|---|---|---|---|
| 4,037,100 A | | 7/1977 | Purser |
| 4,248,830 A | * | 2/1981 | Kallies et al. ................. 422/59 |
| 5,209,919 A | | 5/1993 | Turteltaub et al. |
| 5,261,250 A | | 11/1993 | Missimer |
| 5,314,827 A | | 5/1994 | Schmidt et al. |
| 5,366,721 A | | 11/1994 | Turteltaub et al. |
| 5,376,355 A | | 12/1994 | Turteltaub et al. |
| 5,811,631 A | | 9/1998 | Cripe et al. |
| 6,238,627 B1 | * | 5/2001 | McGowan et al. .......... 422/130 |
| 2002/0066712 A1 | * | 6/2002 | Brockwell ................... 215/247 |

OTHER PUBLICATIONS

Vogel, J. S., et al., "C Background Levels in an Accelerator Mass Spectrometry System," Radiocarbon, vol. 29, No. 3, 1987, pp. 323-333.
Vogel, J. S., et al., "Catalyst and Binder Effects in the Use of Filamentous Graphite for AMS," Nuclear Instruments and Methods in Physics Research B29, 1987, pp. 50-56.
Vogel, J. S., et al., "Performance of Catalytically Condensed Carbon for Use in Accelerator Mass Spectrometry," Nuclear Instruments and Methods in Physics Research B5, 1984, pp. 289-293.
Vogel, J. S., "Rapid Production of Graphite Without Contamination for Biomedical AMS," Radiocarbon, vol. 34, No. 3, 1992, pp. 344-350.
Gadd, G. E., et al., "The World's Smallest Gas Cylinders?," Science, vol. 277, Aug. 15, 1997, pp. 933-936.

* cited by examiner

*Primary Examiner*—Sam P Siefke
(74) *Attorney, Agent, or Firm*—Eddie E. Scott; John H. Lee (57) ABSTRACT

A system for quantitatively reducing oxide gases. A pre-selected amount of zinc is provided in a vial. A tube is provided in the vial. The zinc and the tube are separated. A pre-selected amount of a catalyst is provided in the tube. Oxide gases are injected into the vial. The vial, tube, zinc, catalyst, and the oxide gases are cryogenically cooled. At least a portion of the vial, tube, zinc, catalyst, and oxide gases are heated.

18 Claims, 4 Drawing Sheets

SYSTEM FOR TRAPPING AND STORING GASES FOR SUBSEQUENT CHEMICAL REDUCTION TO SOLIDS

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to chemical reaction of gases with selected catalysts to produce solid materials that may be used for numerous applications, particularly analysis and more particularly to Studying the isotopic makeup of substances.

2. State of Technology

U.S. Pat. No. 4,037,100 for an ultra-sensitive spectrometer for making mass and elemental analyses to Kenneth H. Purser issued Jul. 19, 1977 provides the following background information, " . . . an extremely sensitive apparatus which can be used for the detection of electronegative particles and provide data as to their elemental composition. A mass spectrometer selects negative ions of the required mass coming from an ion source. These ions are then directed into a dissociator which fragments complex molecules and strips electrons from the resulting products producing positively charged ions. These positively charged ions are filtered by a series of elements which independently measure some combination of the quantities: energy/charge, energy, momentum/charge, velocity, charge. Such measurement allows the actual mass of each particle to be uniquely defined and, if necessary, over-determined for reduction of backgrounds."

U.S. Pat. No. 5,209,919 for a method of measurement in biological systems to Kenneth W. Turteltaub issued May 11, 1993 provides the following background information, " . . . a method of quantifying molecular mixtures of and adhesions to minute amounts of biological substances using an accelerator mass spectrometer. Still more particularly, it relates to a process of measurement using intermediate and long lived isotopes bound to biological substances which are then converted to forms suitable for analysis by accelerator mass spectrometry."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a system for quantitatively reducing oxide gases. A pre-selected amount of reductant is provided in a vial. A tube is provided in the vial. The reductant and the tube are separated. A pre-selected amount of a catalyst is provided in the tube. A cap that affords gas transfer to or from the vial is provided. The vial, tube, reductant, and catalyst are cryogenically cooled. Oxide gases are trapped in the vial. At least a portion of the vial, tube, reductant, catalyst, and oxide gases are heated. One embodiment of a system constructed in accordance with the present invention includes a vial; a pre-selected amount of zinc in the vial; a tube in the vial; means for separating the zinc from the tube; a pre-selected amount of a catalyst in the tube; a septa cap that seals the vial; means for cryogenically cooling the vial, tube, zinc, and catalyst; means for injecting oxide gases into the vial; and means for heating at least a portion of the vial, tube, zinc, catalyst, and oxide gases.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Referring now to the drawings, to the following detailed information, and to incorporated materials; a detailed description of the invention, including specific embodiments, is presented. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Figure 1:
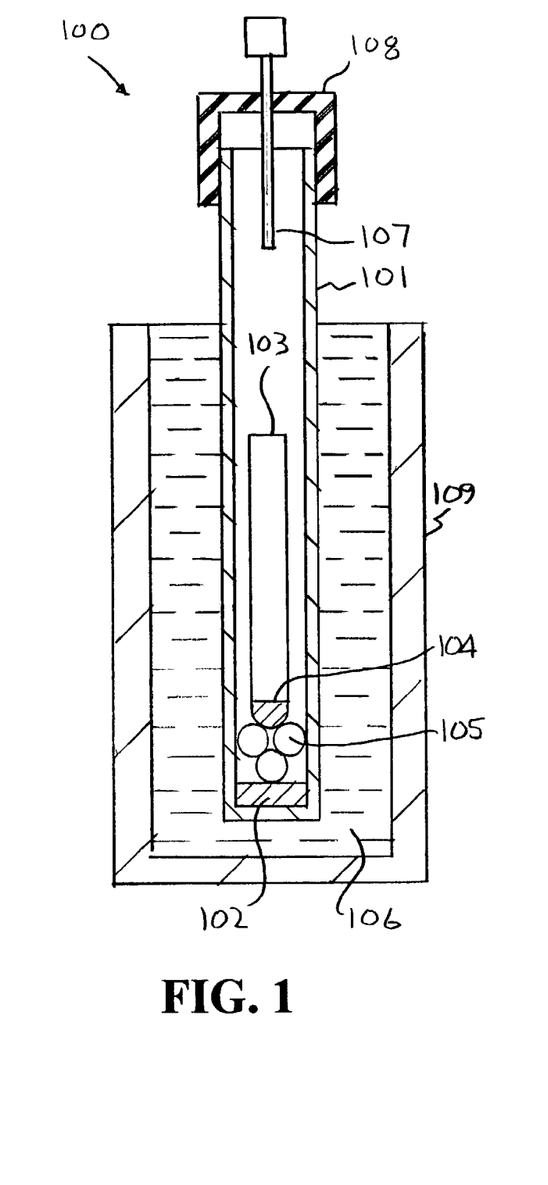
FIG. 1 shows a septa-sealed vial used to trap and store injected gases.

One embodiment of a system constructed in accordance with the present invention is illustrated in FIG. 1. This embodiment is designated generally by the reference numeral 100. A septa-sealed vial 101 is used to trap and store injected gases. These gases can then be chemically reduced to solid form in the septa-sealed vial 101 through direct chemical action and/or through catalytic reactions.

The system 100 provides a way to recover the reacted product in isolation. One use of the system 100 is to trap carbon dioxide from the effluent of a continuous-flow combustion unit for reduction of the CO, to a form of fullerene over an iron or cobalt catalyst that can be used as sample material in an accelerator mass spectrometry system. Carbonaceous biochemical samples can be converted to fullerene for subsequent isotope ratio quantification via accelerator mass spectrometry. The sample preparation apparatus uses disposable materials to limit sample cross contamination. These materials used are inexpensive and readily available. High sample throughput is provided.

In the system 100, gases are cryogenically condensed as they are injected into an evacuated septa-sealed glass vial 101 or as they flow through vial 101 in a stream of carrier gas. The septa-sealed vial 101 will hold the gases with a low loss rate due to leakage. The gases can then undergo chemical reactions to reduce them to solids, wherein they can be stored indefinitely. Tests show that up to 10 atmospheres of gas can be stored with minimal sample leakage over a 24 hour period.

Sample preparation is an important requirement of many analysis and testing systems. The system 100 can be used for the production of graphite for isotope ratio quantification via accelerator mass spectrometry. Mass spectrometry has been used since early in the 1900s to study the chemical and isotopic makeup of substances. A sample is put into a mass spectrometer, which ionizes it and analyzes the motion of the various ions in an electric field to sort them out by their mass-to-charge ratios. The basic principle is that isotopes of different masses move differently in a given electromagnetic field.

In accelerator mass spectrometry, the same principle applies but the process is different. Negative ions made in an ion source are accelerated in a field of millions of volts. The accelerated ions smash through a thin carbon foil or gas that destroys all molecular species. After passing through a high-energy mass spectrometer and various filters, the ions finally slow to a stop in a gas ionization detector. The identity of individual ions can be determined from how the ions slow down. For example, carbon-14 slows down more slowly than nitrogen-14, so those ions of the same mass can be distinguished from one another. Once the charges are determined, the detector can tell to which element each ion belongs and counts the desired isotope as a ratio of a more abundant isotope-carbon-14 as a ratio of carbon-13, for example.

The two "tricks" that make AMS work so well are the molecular dissociation process that occurs in the accelerator and the ion detection at the end. The resulting sensitivity is typically a million times greater than that of conventional isotopic detection. For biological studies, AMS has been used primarily for counting carbon-14 because carbon is present in most molecules of biological interest and carbon-14 is relatively rare in the biosphere. Tritium (hydrogen-3) has also been used extensively as a tracer in biological research. The use of tritium in AMS is new and holds great promise, because many molecules are easier to tag with tritium than with carbon-14. Other isotopes are measured by AMS as well, including plutonium-239, calcium-41, beryllium-10, chlorine-36, and iodine-129. All over the world, AMS is still used primarily to count carbon-14 in archaeological and geologic samples for dating purposes. In the 1980s, it replaced the traditional method of scintillation counting for precise radiocarbon dating, which was time-consuming and required relatively large samples.

Accelerator Mass Spectrometry (AMS) is a mass spectrometric method for quantifying extremely low concentrations of long-lived radioisotopes, such as the commonly used biochemical tracer 14C. AMS can measure attomoles of radiocarbon with a precision of better than 10%. This corresponds to the need for less than 0.1 DPM-equivalent of labeled agent per gram of biological sample. AMS has use when sample is limiting, specific activity is very low, when the level of isotope that can be used is very limited (humans studies) and when trying to study events that occur with very low frequency or at very low concentration.

The system 100 provides a way to recover the reacted product in isolation. The septa-sealed vial 101 contain a small amount of zinc 102 and a small glass tube 103. Inside the tube 103 is a small amount of iron 104. Separating the zinc 102 and the glass tube 101 are small glass beads 105. Carbon dioxide gas and water vapor are injected into septa-sealed vial 101 and cryogenically trapped by liquid nitrogen 106. The needle 107 is removed and the vial 101 is ready for further processing.

Figure 2:
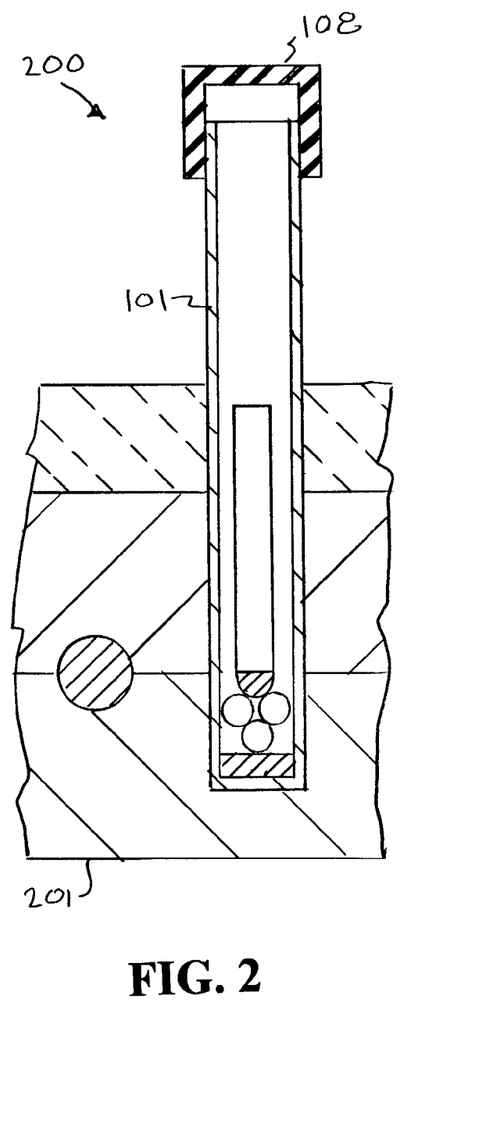
FIG. 2 shows the septa-sealed vial being heated.

Referring now to FIG. 2, septa-sealed vial 101 is shown being heated. The bottom of the vial 101 is placed in a high temperature oven 201. High temperature induces the zinc to reduce the CO2 to CO and the H2O to H2. The CO and H2 react to form a solid fullerene form of carbon on the iron catalyst.

The embodiment 100 for traping and storing gases has many uses. For example the embodiment 100 can be used as a reaction vessel for the chemical reduction of CO gas to solid graphite for quantitative isotope ratio analysis; as a reaction vessel for the chemical reduction of H2 gas to solid TiH2 for quantitative isotope ratio analysis; as a temporary storage vessel of gas; as an integral component of an automated system for the trapping, storage and chemical reduction of gas to solid form for quantitative isotope ratio analysis; as a commercial reaction vessel for the chemical reduction of CO2 gas; and other uses.

Figure 3:
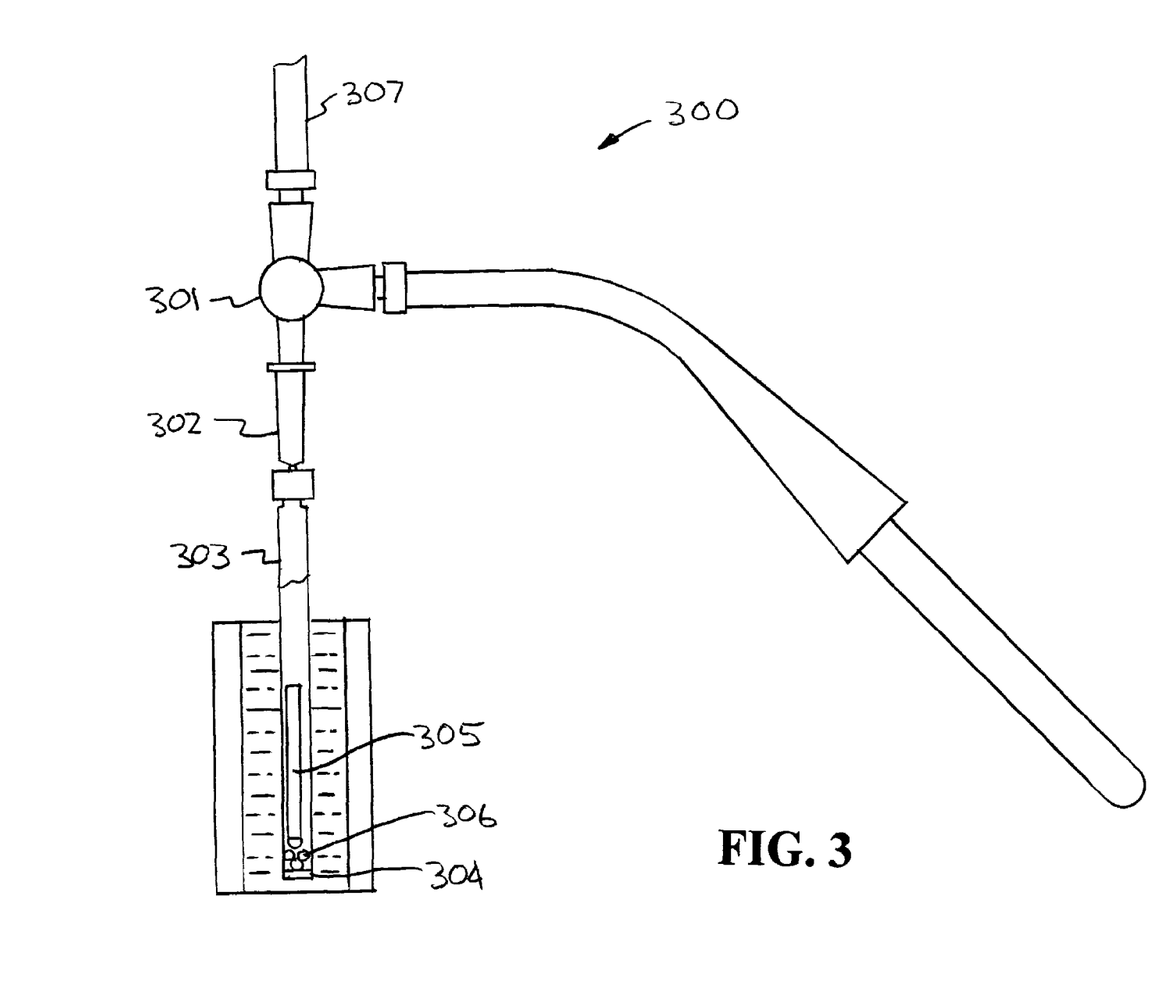
FIG. 3 illustrates a system for converting $CO_2$ obtained from carbonaceous samples to solid graphite for highly sensitive and precise $^{14}C$ quantification.

Referring now to FIG. 3, another embodiment of a system constructed in accordance with the present invention is illustrated. This embodiment is designated generally by the reference numeral 300. The embodiment 300 provides a system for converting $CO_2$ obtained from carbonaceous samples to solid graphite for highly sensitive and precise $^{14}C$ quantification. Septa-sealed vials are used along with commercially available disposable materials, eliminating sample cross contamination, minimizing complex handling and keeping per sample costs low. Samples containing between 0.25 and 10 mg total carbon can be reduced to graphite in approximately 4 hours in routine operation. Approximately 150 samples per 8-hour day can be prepared by a single technician. The samples are used for analysis and testing. For example the samples can be used for accelerator mass spectrometry. The growth of accelerator mass spectrometry as a tool for quantitative isotope ratio analysis in the biosciences necessitates high throughput sample preparation.

Accelerator mass spectrometry (AMS) is a highly sensitive isotope ratio spectrometer that uses a high voltage accelerator to destroy interfering molecular isobars. Attomole ($10^{-18}$) amounts of $^{14}C$ can be quantified, with high precision, in submilligram-sized biochemical samples (e.g. 25 µl of blood). Small sample sizes permit expanded experimental resolution through frequent blood draws, extensive chemical fractionation and/or selective biological dissection. This sensitivity allows the detailed tracing of nutrients, toxins and therapeutics in humans and animals with less than µg/kg chemical doses containing nanoCurie (nCi) exposures to $^{14}C$. Hundreds of samples whose $^{14}C$ levels can vary over several orders of magnitude can be generated. Methods for preparing samples for measurement need to be high throughput processes in which cross contamination is eliminated through careful design protocols. Per sample costs need to be kept low and human intervention minimized. Additionally, the method needs to be able to treat the wide variety of biological matrices equally to insure the chemical and physical equivalence for all carbon atoms in the samples. For $^{14}C$-AMS, solid graphite is used most often as the sample material for quantification, although gaseous $CO_2$ is also used.

The injection. of $CO_2$ into an ion source enables the direct coupling of separatory techniques, such as a gas chromatograph, to the spectrometer making the most efficient use of the sample. However, gas-$CO_2$ ion sources generate small negative ion currents needed for AMS and exhibit short term memory effects, limiting their usefulness for high throughput quantification. Solid graphitic samples are ionized by Cs-sputter ion sources to generate intense negative ion currents with 4-10% efficiency. Low memory effects between solid samples allow for the fast switching from one sample to the next, enabling high throughput. Graphite has no "vapor pressure" which makes sample handling easier and reduces contamination of equipment and other samples by "hot" samples (>10 fmol $^{14}C$/mg C). Finally, the separation of the sample preparation and measurement processes allows for a more efficient use of the spectrometer. Biochemical samples can be converted to graphite independent of the relatively faster AMS measurement, and investigators can retain chemical control of their samples right through the conversion to an inert form.

Graphite samples are prepared by the reduction of carbon dioxide by hydrogen onto a catalytic iron surface at temperatures around 500° C. Variations on the chemistry include the addition of zinc and the replacement of iron with cobalt. Reduction of $CO_2$ to a Fullerene "graphite" proceeds rapidly and yields of >95% are obtained. Samples containing as little as 20 µg carbon can be converted to graphite. The graphite quickly produces intense, long-lasting negative ion beams upon introduction to the cesium sputter ion source. Isotopic and mass fractionation are extremely small.

Table 1 shows relevant chemical reactions for the reduction of carbon dioxide to graphite over an iron catalyst at temperatures between 450° C. and 650° C.

TABLE 1

$$CO_2 + Zn \longleftrightarrow CO + ZnO \quad (1)$$

$$H_2O + Zn \longleftrightarrow H_2 + ZnO \quad (2)$$

$$CO_2 + H_2 \longleftrightarrow CO + H_2O \quad (3)$$

$$2CO \xrightarrow{Fe} C_{gr} + CO_2 \quad (4)$$

$$CO + H_2 \xrightarrow{Fe} C_{gr} + H_2O \quad (5)$$

$$CO + 3H_2 \longleftrightarrow CH_4 + H_2O \quad (6)$$

$$2CO + 2H_2 \longleftrightarrow CO_2 + CH_4 \quad (7)$$

The reductions of $CO_2$ to CO and $H_2O$ to $H_2$ by Zn as shown by reactions (1) and (2) in Table 1 are thermodynamically favored and proceed quickly. Carbon dioxide can also be reduced to carbon monoxide by hydrogen gas as shown in reaction (3). In the absence of both zinc and hydrogen gas, carbon dioxide does not reduce to graphite with sufficient yield as the catalytic surfaces of the iron becomes deactivated through the formation of iron oxides. Importantly, zinc also reduces sulfur dioxide, present from the combustion of sulfur-containing compounds, by forming zinc sulfide. The presence of sulfur slows down and will eventually quench the deposition of graphite by inactivating the surface of the catalyst, most likely through the formation of pyrrhotite (FeS).

Equations (4) and (5) in Table 1 show the two graphite-forming reactions from carbon monoxide in the presence of an iron catalyst. Cobalt and nickel are also effective catalysts between 450° C. and 650° C. Graphite deposition proceeds rapidly in the presence of sufficient $H_2$. The reaction initiates as carbon monoxide, chemisorbs onto the surface of the iron, and then dissociates with the loss of the oxygen to $H_2$ or gaseous CO. The carbidic carbon diffuses through the iron and either precipitates as filamentous graphite or forms cementite ($Fe_3C$). Graphitization ceases when all the carbon has precipitated as Fullerene, or the catalyst has lost activity by being completely carbided to cementite or oxidized to iron oxide. Cesium sputtering of iron carbide yields only 3% the $C^-$ beam than that from graphite. Consequently, $^{14}C$-AMS solid sample preparation uses an excess of fine mesh iron to ensure an abundance of catalytic surfaces.

The rate of carbon deposition is significant between 500° C. and 800° C. At higher temperatures, sintering of the iron catalyst retards carbon deposition. At lower temperatures, graphitization is hindered by the incomplete dissociation of $Fe_3C$. Additionally, Fischer-Tropsch reactions lead to the synthesis of methane as shown by reactions (6) and (7) in Table 1 at temperatures below 450° C., or in the presence of large amounts of hydrogen gas. Methane will decompose to graphite, but only in appreciable amounts above 900° C. with large isotopic fractionation.

One of the Applicants developed a method for the rapid production of filamentous graphite from carbonaceous biochemical samples. The method uses disposable gas manifolds to transfer combustion products to a borosilicate tube which is sealed by a torch for subsequent reduction of the $CO_2$ to graphite. Conversion yield is approximately 80%, with bulk isotopic fractionation in the finished graphite less than 0.5%. With this method, 300 samples/week/technician can be processed and our laboratory has prepared over 60,000 samples. The use of disposable materials minimizes sample cross contamination. However, the torch-sealing of the transferred combustion products necessitates dexterous handling, is somewhat time-consuming, and uses custom-made components.

The embodiment 300 illustrates a method for preparing filamentous graphite from $CO_2$ gas in septa-sealed vials. This method increases sample preparation throughput while maintaining success in graphite preparation. This method also reduces the amount and complexity of handling required with each sample, which leads to lower process backgrounds and allows for the preparation of smaller sized samples. The use of septa-sealed vials forms the basis for an integrated automated system in which biochemical samples can be converted to graphite for $^{14}C$-quantification via AMS.

Description of system 300.—The biochemical sample is dried in a vacuum centrifuge in a new 6 mm×50 mm quartz glass culture tube. A few milligrams of wire-form cupric oxide are added to the dried sample and the culture tube is placed inside a 9 mm×150 mm quartz combustion tube which has a break-seal point. The tubes are flamed-sealed under vacuum and placed in a 900° C. furnace for 2 hours. After heating, the cooled tube is connected to a Luer-Lok stopcock 301 with ½" i.d. bubble tubing (Oxford Labware), as depicted in FIG. 1. A small amount of silicone grease produces a vacuum-tight seal between the glass tube and the plastic tubing. Attached to one end of the stopcock is a 26 gauge needle 302 which is inserted into the 8×80 mm septa-sealed borosilicate glass vial 303 containing a small amount of zinc dust 304 (Sigma-Aldrich; 20,998-8) and a 3 mm i.d.×30 mm long borosilicate glass tube 305 (Scientific Instrument Services, Ringoes, N.J.; SPV5000). Inside the tube is 2-3 mg of −400 mesh iron powder (Sigma-Aldrich; 25,563-7). Separating the glass tube and the zinc are several 3 mm borosilicate glass beads 306. After evacuation, the valve is closed to isolate the system from the vacuum pump 307 and the tip of the combustion tube is broken. More than 95% of the condensable combustion products (mainly, $CO_2$ and $H_2O$) are cryogenically trapped into the septa-sealed vial in less than 20 seconds. Non-condensing gases, such as $N_2$, are then removed by the vacuum pump. The vial is pulled off the needle and the lower 3 cm is inserted into a block heater held at 500° C. The amount of methane formed at low temperatures is reduced by the direct insertion of the cold vial into the pre-heated block.

Figure 4:
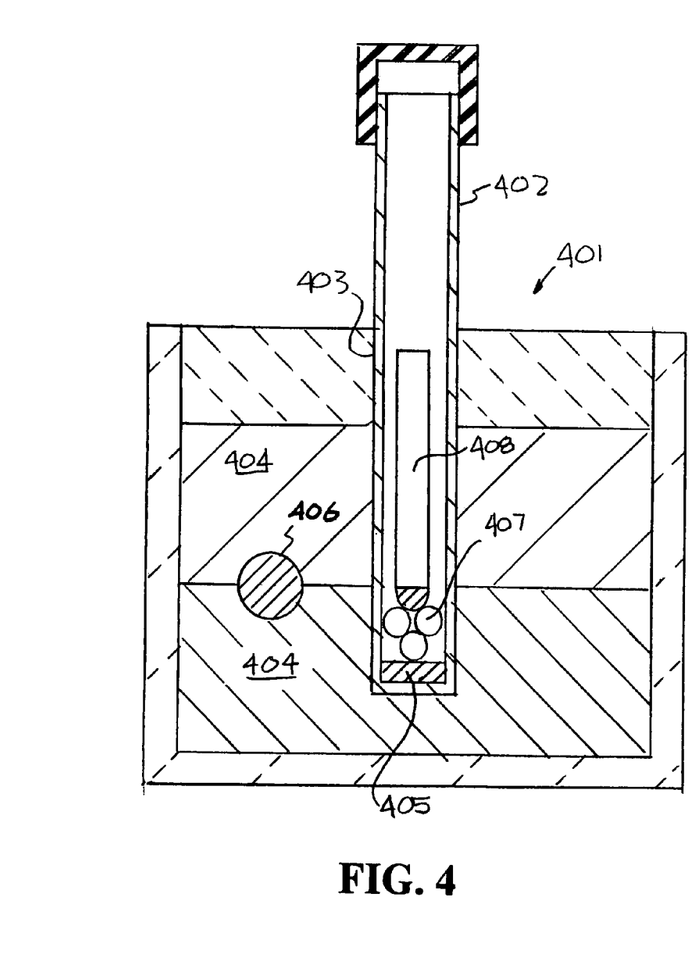
FIG. 4 is a cross sectional view of a reduction heater.

A cross sectional view of the reduction heater 401 is shown in FIG. 4. The vial 402 sits in holes 403 drilled into two 1.3 cm thick copper blocks 404 that have been plated with 0.13 mm nickel. Approximately 5 cm of vial remains above the reduction oven surface to prevent heating of the septa. At this distance, without additional cooling, the septa remain only slightly warm to the touch, while the bottom 405 3 cm of the vial is heated to 500° C. Copper is an excellent thermal conductor and is easily machined. Nickel-plating impedes the formation of CuO and $Cu_2O$ which are formed in copious amounts when heated copper is exposed to air. The copper blocks are insulated on the sides and bottom by 6-10 cm of machinable ceramic (Cotronics, Brooklyn, N.Y.; RESCOR™ 310) and on the top by a 13 mm thick ceramic foam board (Cotronics, Brooklyn, N.Y.; RESCOR™ 360). Heat is supplied by 400 W (@120 VAC) 9.5 mm diameter Firerod® cartridge heaters 406 (Watlow, St. Louis, Mo.). Temperature regulation is through a K-type thermocouple inserted into one of the holes normally occupied by a vial. The output of the thermocouple serves as the input to a temperature controller (Watlow, St. Louis, Mo.; Series 935) which drives a 120 VAC solid state relay to supply up to 1200 W of power to the heating elements. Although only one heater 406 and one vial 402 is shown, each 12 inch long heat rod can accommodate multiple vials. An oven, which consists of two heat rods to heat 67 samples, reaches its normal operating temperature of 500° C. in 30 minutes. Glass tube 408 is supported inside vial 402 by glass beads 407.

The 8×80 mm long septa-sealed glass vials 402 were produced from Applicants' design by Kimble Kontes Scientific Glassware, Vineland, N.J. The vials are overcrimped and PTFE/Silicon septa are used to minimize losses due to leakage. Under these conditions, the vials will hold up to 10 atm of carbon dioxide gas (~11 mg in the 2.25 ml volume at room temperature) with a very low leak rate (typically a few percent per hour at the highest pressures). Reduction temperatures are kept below 600° C. to prevent gas pressure from causing extreme deformation of the glass vials which impedes their removal from the oven.

All materials shown in FIGS. 3 and 4 that come into direct contact with the sample are disposable and commercially available with a total cost of approximately $5.50 USD per sample; $3 USD of which is due to the quartz glass combustion tubes. Heretofore, the materials cost were approximately $9 USD per sample.

Graphitization of the sample is >95% complete in less than 4 hours. The graphite/iron mixture is then pounded into a 2.5 mm deep hole drilled into a 9.5 mm×29 mm long aluminum target with a fresh #55 drill stem. The $^{14}C/^{13}C$ isotope ratio is quantified by accelerator mass spectrometry. Details of our spectrometer are presented elsewhere. In general, 3 to 7 replicate measurements of either 10000 $^{14}C$ counts or 30 seconds analysis time are conducted to obtain at least 3% precision. As AMS measures isotope ratios, all measurements are normalized to similarly prepared and measured standards of known carbon isotope ratios. The biosciences AMS program at Lawrence Livermore National Laboratory uses graphitized ANU (Australian National University) sucrose, with an accepted $^{14}C/C$ ratio of 1.5081 Modern as the primary standard. The unit Modern is a well-defined number equal to a $^{14}C/C$ isotope ratio of $1.180\times10^{-12}$ which is close to the naturally occurring $^{14}C$ concentration in the biosphere. This unit is also equivalent to 97.8 amol/mg C and 6.11 fCi/mg C.

Experiments—While the basic chemistry of the reduction process remains the same, Applicants developed modifications to the previous preparation procedures. Hydrogen increases throughput by shortening the reduction time in the vial, but excess hydrogen can lead to methane production and loss of quantitative conversion. Applicants sought a balance of these effects in a robust, reproducible method. Applicants compared three methods of introducing hydrogen to the combustion products to speed up the reduction of $CO_2$: 1) the addition of a measured amount of hydrogen gas; 2) the addition of $TiH_2$; and 3) retention of $H_2O$ from the combusted sample.

Method 1 requires a priori knowledge of the amount of carbon in the combusted sample to insure the correct stoichiometric ratio of C to H for efficient graphitization by introducing the correct amount of $H_2$ gas. The nondestructive measurement of the $CO_2$ in the sample involves expansion of the gas into a non-disposable calibrated volume and measured with a pressure transducer. The expanded gas is then quantitatively recondensed into the reduction vial and a measured amount of hydrogen gas is added. Applicants used this method to quantify graphite production, but it requires more sample handling which adversely affects sample throughput and introduces the possibility of sample carry-over in the calibrated volume.

Method 2 takes advantage of the fact that hydrogen gas is released from trapped sites within the titanium crystal structure upon heating. All water is removed from the combusted sample to control the final $H_2$ content. Either the bottom of the combustion tube or a portion of the bubble tubing transfer line is immersed in a dry ice-slush bath to freeze out water formed during the combustion of the sample. Only a small amount of $TiH_2$ is required to produce rapid reduction, since Zn reduces $CO_2$ to CO to form significant reducing potential. One of the applicants used 10-40 mg $TiH_2$ per mg carbon and more caused the reduction yield to drop. Applicants found with the septa-sealed vials, that the less $TiH_2$ added, the higher the graphite yield (measured as analyzed $^{13}C^+$ current), indicating that only the smallest amounts ($\leq$10 mg $TiH_2$/mg C) are required. It is also possible that some of the water from the combusted sample is not retained by the dry-ice slush bath and is transferred along with the $CO_2$ into the septa-sealed vial. This water, upon its reduction by zinc, is a source of hydrogen gas. Depending on the amount of water transferred and the quantity of $TiH_2$, there exists the possibility for excess $H_2$ gas, leading to the loss of quantitative graphite yield.

Method 3 exploits the hydrogen present in carbonaceous biochemical samples. For example, dried biological tissue can be roughly approximated by the chemical formula $C_5H_9O_2N$. This is an adequate amount of hydrogen, as long as sufficient zinc is present in the sample to dissociate the water formed during combustion and reduction. The samples are dried before combustion, removing any excess of hydrogen from wet tissues. In practice, it is easier to transfer most of the water from the combustion tube than to prevent most of it from transferring. Retention of the water for use as a reductant worked well for this application, but it may not be compatible with tissue samples that are not dried before combustion or when conducting a $^{14}C$, $^3H$ dual-labeling experiment. In the case of the former, there might be too much hydrogen present, while in the latter, the water is separately trapped for tritium-AMS quantification Applicants determined the range of carbon masses that can be routinely prepared in septa-sealed vials. Additionally, Applicants verified that the graphite produced by this method continues to yield the high precision and high accuracy measurement capabilities of AMS.

Figure 5:
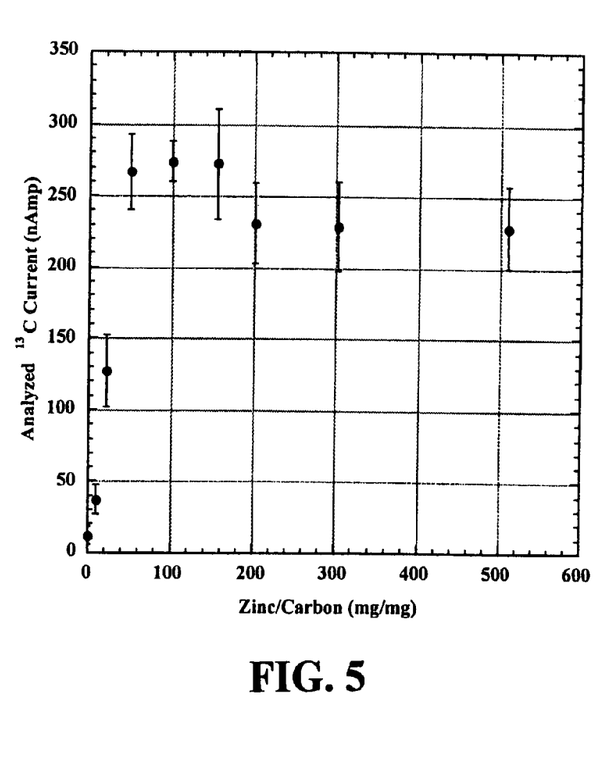
FIG. 5 shows a plot of analyzed $^{13}C^+$ current for graphitized sucrose containing 0.5 mg carbon as the amount of zinc metal powder was varied.

FIG. 5 shows a plot of analyzed $^{13}C^+$ current for graphitized sucrose containing 0.5 mg carbon as the amount of zinc metal powder was varied. All other conditions were kept constant. Approximately 75-150 mg zinc per mg carbon maximizes satisfactory graphite production. This is much more than would be expected from stoichiometry. However, it is clear that not all the zinc gets converted to ZnO. The vapor pressure of zinc at 500° C. is approximately 0.4 kPa. As the vaporous zinc flows away from the heated bottom of the vial, it will recondense when it reaches the cooler upper regions. A thick band of zinc metal forms on the inside of the septa-sealed vials near the top of the foam insulator sheet, extending 1 to 2 cm downward. Excessive quantities of zinc increased the thickness of this band to the extent that some of the zinc would be incorporated into the graphite/iron mixture in the bottom of the inner glass tube. The presence of zinc in the graphite decreases sputtering yields in the ion source. In some cases, the inner vial would be trapped in the resolidified zinc metal, preventing recovery of the graphite sample. The addition of the 3 mm glass beads elevates and separates the glass vial from the zinc metal.

Figure 6:
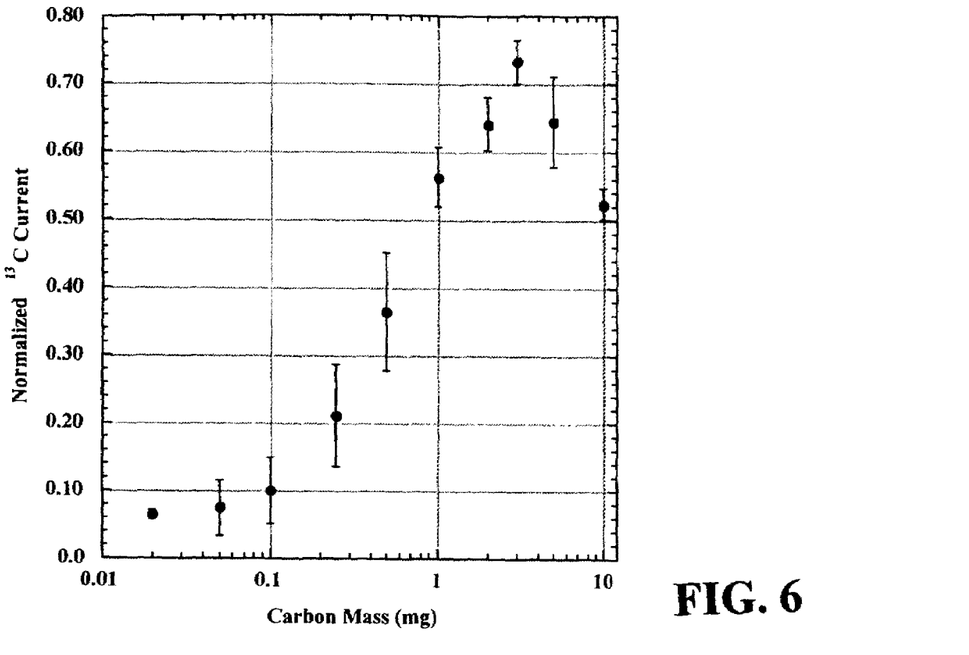
FIG. 6 shows a plot of analyzed $^{13}C^+$ current of graphite with respect to precombusted carbon mass of sucrose samples with all other conditions kept fixed.
Figure 7:
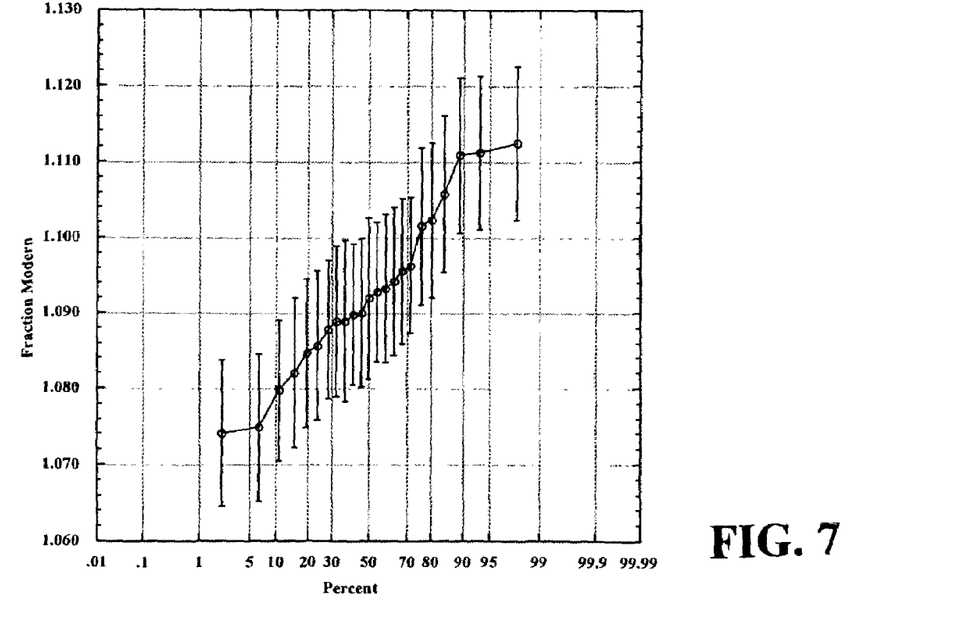
FIG. 7 shows a probability plot of the Fraction Modern determined from the measured $^{14}C/^{13}C$ isotope ratios.

Carbon Mass Range.—FIG. 6 shows a plot of analyzed $^{13}C^+$ current of graphite with respect to precombusted carbon mass of sucrose samples with all other conditions (i.e., amount of zinc, reduction time and temperature) kept fixed. The ion current was normalized to the $^{13}C^+$ current from ANU sucrose standards containing 1 mg carbon. For large sample masses, geometrical factors of the cathode and the cesium sputter ion beam prevent an ever-increasing output current as the amount of graphite increases. It is also possible that there is insufficient zinc in the reduction vial to maximize graphite yield. Dilution of the iron with graphite reduces the thermal and electrical conductivities of the iron/graphite mixture, limiting the effectiveness of the sputtering process. As the amount of carbon in the sample decreases, the ion current goes to a maximum as the optimal iron to graphite ratio is obtained. After this maximum, the analyzed current drops as dilution of the graphite with excess iron limits sputtering efficiency. This trend, however, does not continue and another mechanism must be invoked to explain the results seen for the smallest samples. There is no pretreatment of the iron to remove dissolved or absorbed atmospheric $CO_2$. This background carbon dioxide, albeit at small levels, may be reduced along with the carbon dioxide from the combusted sucrose sample, effectively raising the graphite yield. The measured carbon isotope ratios of this graphite is not significantly different from that of the larger mass samples, as both sources have nearly Modern levels of $^{14}C$.

The data indicate that a routine procedure in the preparation of samples containing at least 250 µg of carbon can produce graphite in sufficient yields for $^{14}C$-quantification via AMS. Samples containing more than 10 mg of carbon risk loss through explosive overpressurization of the 9×150 mm sealed combustion tubes, or excessive leakage of the septa-sealed vials. While graphite has been produced from samples containing <250 µg carbon, the ion currents were sufficiently low that high measurement throughput would be compromised. Special techniques are required to maximize yield and ion source output. These might include the use of smaller septa-sealed vials, a corresponding lesser amount of reactants, and pretreatment of the iron catalyst.

Reproducibility and Reliability.—Twenty three individual samples of mouse livers, each containing between 2 and 10 mg carbon were combusted and subsequently converted to graphite. FIG. 5 shows a probability plot of the Fraction Modern determined from the measured $^{14}C/^{13}C$ isotope ratios. The data fits a normal Gaussian distribution with a high correlation coefficient (r=0.99), indicating that the data set represents a single distribution. That distribution has a mean of 1.0928 Modern and a standard deviation of 0.0107 or 0.98%. This width is approximately equal to the average of the error bars on the individual data points. These data confirm that the new technique is able to produce graphite from individual identical biological samples reliably and with a high degree of reproducibility.

Comparisons of Carbonaceous Material.—Six samples of tributyrin (ICN Pharmaceuticals, Inc.; 10311), sucrose (Sigma-Aldrich; S-9378), ANU sucrose and $^{14}C$-elevated plant extract, each containing between 2 and 10 mg carbon each were combusted in sealed quartz tubes. Three of each were transferred to and reduced to graphite in septa-sealed vials while graphite from three of each was prepared in torch-sealed tubes. The $^{14}C/^{13}C$ isotope ratios of all samples were measured by AMS. These four samples were chosen as their $^{14}C$ levels span the range of the majority of biochemical samples typically measured by AMS. The results of this comparison are presented in Table 2. The last column shows the percent difference in the averages for each method with a positive value indicating that the torch-sealed method gave a higher Fraction Modern. The torch-sealing method gave relatively high values for the Fraction Modern values compared to the septa-sealed vials for the tributyrin sample. A plausible explanation for this is that less background contamination is present in the septa-sealed vials. The vials have less surface area than the tubes used for torch-sealing which could lower the amount of ambient $CO_2$ that gets absorbed onto the glass. This $CO_2$, which would have modern levels of $^{14}C$, would be desorbed at high temperatures and reduced to graphite during the reduction.

TABLE 2

Fraction Modern values and % differences for a group of samples prepared through torch-sealed tubes and septa-sealed vials.

| | Average Fraction Modern | | Difference |
|---|---|---|---|
| Sample | Torch-Sealed | Septa-Sealed | (%) |
| Tributyrin | 0.0891 ± 0.0010 | 0.0854 ± 0.0018 | 4.2 |
| Sucrose | 1.1316 ± 0.0052 | 1.1367 ± 0.0075 | −0.5 |
| ANU sucrose | 1.5179 ± 0.0074 | 1.5105 ± 0.0011 | 0.5 |
| Plant extract | 9.1748 ± 0.1530 | 9.3784 ± 0.0935 | −2.2 |

The embodiments described above illustrate a system in which $CO_2$ from biochemical samples is transferred to and reduced to graphite in septa-sealed vials for $^{14}C$ measurement by accelerator mass spectrometry. A single recipe is employed to prepare samples with a range of carbon between 0.25 and 10 milligrams and that span a wide range of $^{14}C$ levels. Sample cross contamination is eliminated through the extensive use of disposable Luer accessories and tubing with relatively low costs per sample. The system is amenable to high throughput as over 150 samples per eight-hour day can be processed by a single technician. Septa-sealed vials form the basis for an automated sample preparation system in which combustion products from a commercial carbon analyzer is trapped and subsequently reduced to graphite. Such automated processes greatly improves throughput and reduce the amount to sample handling leading to the routine preparation of samples as little as 20 µg carbon.

Other embodiments illustrate systems for quantitatively reducing oxide gases, comprising a vial; a pre-selected amount of reductant in the vial; a tube in the vial; means for separating the reductant and the tube; a pre-selected amount of a catalyst in the tube; a closure for the vial that allows gas transfer in and out of the vial; means for trapping the oxide gases in the vial; and means for heating at least a portion of the vial, the tube, the reductant, the catalyst, and the oxide gases. In one embodiment the means for trapping the oxide gases in the vial includes means for cryogenically cooling the vial, the tube, the reductant, the catalyst, and the oxide gases.

In another embodiment the oxide gases include products of combustion. In another embodiment the oxide gases include carbon dioxide gas. In another embodiment the oxide gases include water vapor. In another embodiment the oxide gases contain a sample to be analyzed.

In another embodiment the reductant is zinc. In another embodiment the reductant is hydrogen gas. In another embodiment the catalyst is cobalt. In another embodiment the catalyst is iron. In another embodiment the means for separating the reductant and the tube is a multiplicity of glass beads separating the reductant and the tube.

In another embodiment the vial is a reaction vial of sufficient size to contain the oxide gases at room temperature and at whatever temperature is required for additional chemical reactions to proceed. In another embodiment the vial includes a piercable septa seal. In another embodiment the vial includes reactant solids or liquids contained in the vial. In another embodiment the vial is an 80 mm×8 mm septa-capped borosilicate vial.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An apparatus for quantitatively reducing oxide gases, comprising:
 a vial, said vial having an upper section and a lower section;
 a pre-selected amount of reductant in said lower section of said vial;
 a tube in said lower section of said vial;
 a multiplicity of glass beads in said lower section of said vial located above said reductant and below said tube, said glass beads separating said reductant and said tube;
 a pre-selected amount of a catalyst in said tube;
 a closure for said vial that allows gas transfer in and out of said vial;
 means for trapping said oxide gases in said vial; and
 a heater for heating said lower section of said vial, said tube, said reductant, said catalyst, and said oxide gases, said heater surrounding said lower section of said vial, said heater comprising
 a first copper block,
 a second copper block with
 a hole in said first copper block and said second copper block with said hole having a depth to receive said lower section of said vial so that said first copper block together with said second copper block surrounds said lower section of said vial wherein said upper section of said vial extends above said hole and said first copper block and said second copper block, and said lower section of said vial extends into said hole, and
 a heating element between said first copper block and said second copper block for heating said first copper block, said second copper block, and said lower section of said vial, said tube, said reductant, said catalyst, and said oxide gases.

2. The apparatus of claim 1, wherein said means for trapping said oxide gases in said vial includes means for cryogenically cooling said vial, said tube, said reductant, said catalyst, and said oxide gases.

3. The apparatus of claim 1, wherein said oxide gases include products of combustion.

4. The apparatus of claim 1, wherein said oxide gases include carbon dioxide gas.

5. The apparatus of claim 1, wherein said oxide gases include water vapor.

6. The apparatus of claim 1, wherein said oxide gases contain a sample to be analyzed.

7. The apparatus of claim 1, wherein said vial is a glass vial.

8. The apparatus of claim 1, wherein said vial is a quartz glass vial.

9. The apparatus of claim 1, wherein said vial is a septa-sealed vial.

10. The apparatus of claim 1, wherein said tube is a glass tube.

11. The apparatus of claim 1, wherein said reductant is zinc.

12. The apparatus of claim 1, wherein said reductant is hydrogen gas.

13. The apparatus of claim 1, wherein said catalyst is cobalt.

14. The apparatus of claim 1, wherein said catalyst is iron.

15. The apparatus of claim 1, wherein said vial is a reaction vial of sufficient size to contain said oxide gases at room temperature and at whatever temperature is required for additional chemical reactions to proceed.

16. The apparatus of claim 1, wherein said vial includes a piercable septa seal.

17. The apparatus of claim 1, wherein said vial includes reactant solids or liquids contained in said via.

18. The apparatus of claim 1, wherein said vial is an 80 mm×8 mm septa-capped borosilicate vial.

* * * * *